United States Patent [19]

Kuch et al.

[11] 4,255,601

[45] Mar. 10, 1981

[54] PROCESS FOR MAKING INDENE

[75] Inventors: Philip L. Kuch, Aurora; Daniel R. Herrington, Warrensville, both of Ohio

[73] Assignee: The Standard Oil Company, Cleveland, Ohio

[21] Appl. No.: 78,121

[22] Filed: Sep. 24, 1979

[51] Int. Cl.$^3$ .......................... C07C 2/66; C07C 2/84; C07C 13/465
[52] U.S. Cl. ................................. 585/411; 585/419; 585/422; 252/431 P
[58] Field of Search ........................... 585/436, 441; 252/429 R; 260/430

[56] References Cited

U.S. PATENT DOCUMENTS

| | | | |
|---|---|---|---|
| 2,531,328 | 11/1950 | Elwell | 585/411 |
| 2,823,240 | 2/1958 | Field et al. | 585/411 |
| 2,916,529 | 12/1959 | Sanford et al. | 585/411 |
| 3,223,742 | 12/1965 | Eberhardt | 585/411 |
| 3,674,884 | 7/1972 | Moritani et al. | 585/436 X |
| 3,775,511 | 11/1973 | Shue | 585/436 X |

*Primary Examiner*—Delbert E. Gantz
*Assistant Examiner*—G. E. Schmitkons
*Attorney, Agent, or Firm*—John E. Miller, Jr.; Herbert D. Knudsen; Larry W. Evans

[57] ABSTRACT

Propylene and benzene are directly reacted in a single step process for making indene by means of a liquid phase catalytic reaction using a gold complex as the catalyst.

13 Claims, No Drawings

PROCESS FOR MAKING INDENE

BACKGROUND OF THE INVENTION

The present invention relates to a novel one-step process for making indene.

A number of techniques are known for making indene. The most common route is via a Diels-Alder addition of cyclopentadiene to butadiene to generate tetrahydroindene which is dehydrogenated to yield indene. Indene may also be obtained from coal tar.

The Diels-Alder route to indene is disadvantageous because it is a two-step process, while it is extremely difficult to obtain pure indene (required for polymerization) from coal tar.

Accordingly, it is an object of the present invention to provide a new one-step direct route for producing indene recoverable in highly pure form.

SUMMARY OF THE INVENTION

This and other objects are accomplished by the present invention which is based on the discovery that propylene and benzene will react together to directly produce indene in a one-step liquid phase process using gold complexes as the reaction catalysts.

Thus, the present invention provides a novel process for producing indene comprising contacting benzene and propylene together in a liquid medium containing a transition metal complex of a metal selected from the group consisting of Au, Ag, Rh, Cu, Ir, Hg, Ni, Ru, Pt, Pd and Os.

DETAILED DESCRIPTION

The reaction involved in this invention is the coupling and cyclization of benzene and propylene in the liquid phase to yield indene as shown in reaction (1) below.

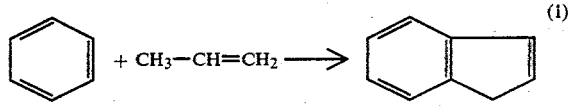

(1)

While indene is a major product of the reaction, the process is not completely selective. The two major by-products are styrene and alpha-methylstyrene.

The reaction is carried out in the liquid phase. The reaction solvent may be any organic solvent which satisfies the criteria of (1) dissolving the catalyst, (2) remaining liquid at the reaction temperatures and pressures, (3) remaining inert to oxidative degradation or side reactions, and (4) being rigorously non-coordinating so as not to bind to active sites of the catalyst. In a preferred embodiment, benzene itself is used as the solvent. This allows for ready recycle of unreacted benzene and eliminates the need for an additional chemical.

The amounts of benzene and propylene in the reaction system can vary widely, and essentially any amount of either reactant can be included in the reaction system. Since benzene will normally be used as the reaction medium, however, a significant excess of benzene is preferred. When benzene is not the reaction solvent, the benzene/propylene ratio is preferably 5/95 to 95/5, more preferably 60/40 to 40/60.

The reaction may be carried out in the presence or absence of oxygen. If oxygen is included in the reaction system, it can be present in any amounts. However, since oxygen and propylene in certain proportions form an explosive mixture, it is desirable that the amount of oxygen be such that the reaction system is outside the explosive range. Most preferably, the propylene/oxygen ratio should be greater than 60% since this is outside the explosive range yet still sufficient to provide an economical process. Moreover, if oxygen is included in the reaction system, the preferred source of the oxygen is air. If oxygen is not included in the reaction system, then the reaction is desirably run at the highest possible ratio of propylene/benzene to ensure maximum indene yields.

While other materials may be included in the reaction system, it is preferred that the reaction system be free of materials (e.g. carbon monoxide) which act as ligands with respect to the M element of the catalyst. Such materials would cause a decrease in catalytic activity and hence impede the reaction.

The reaction may be carried out in the static mode (i.e. in a sealed reactor containing a fixed amount of the reactants) or in a dynamic mode in which propylene and air or $O_2$ are continuously fed into a vessel containing the liquid phase. Indene formation appears to be kinetically slow. Such reactions require relatively long reaction times, and for this reason the static mode is preferred.

Reaction times may vary from 0.5 to 24 hours, preferably 1 to 10 hours. The reaction temperature is preferably in the range of 20° C. to 400° C., most preferably 50° C. to 300° C. Any reaction pressure can be used. Preferably, the reaction pressure is from 1 to 100 atmospheres, more preferably 5 to 75 atmospheres. Higher pressures favor the formation of indene.

The catalysts used in the inventive process are metal complexes of neutral, unipositive and dipositive metals. The catalyst should contain a minimum of two vacant adjacent coordination sites. Preferably, the more "naked" the metal center (i.e. the higher the degree of coordinative unsaturation), the more active the catalyst will be. The stereochemical hindrance about the metal center should be at a minumum and the electropositive nature of the metal at a maximum without sacrificing catalyst stability. Thus, cationic configurations are preferred. The chemical nature of the ligands on the metal is not critical so long as they serve to stablize the metal against decomposition. In this regard, the ligands should be either monomolecular ligands which solubilize the complex or macromolecular ligands such as functionalized polymer, $SiO_2$ or $Al_2O_3$ which render the complex immobile and insoluble, or combinations of the two. In the case of supported metal complexes, these are slurried in the reaction medium.

Catalysts useful in the inventive process can be defined by the following formula

wherein
  M is a neutral, unipositive or dipositive metal selected from the group consisting of Au, Ag, Rh, Cu, Ir, Hg, Ni, Ru, Pt, Pd and Os;
  X is a uninegative coordinating anion;
  L is a neutral coordinating $\pi$-acid type ligand;
  Y is a uninegative non-coordinating anion; and
wherein when
  M is neutral, N=1-6; and
wherein when M is unipositive, $z=0$ or 1; $m=0$ or 1; $m+z=1$; and $n=1$ to 4; and wherein when M is dipositive, $z=0$, 1 or 2; $m=0$, 1 or 2; $m+z=2$; and $n=0$ to 6.

Preferred catalysts are those in which M is unipositive, and more preferred catalysts are those in which M is Au. Of these catalysts, preferred catalysts are those which are ionic (i.e. m is 0 and z equals 1) and of these catalysts the single coordinate catalysts (i.e. n equals 1) are most preferred. Particularly preferred catalysts are those defined by the formula

[ML][Y]

wherein

M is Au;

L is $P\phi_3$, $PMe_3$, $PEt_3$, $P(C_6H_{11})_3$, $As\phi_3$, $AsEt_3$, $Sb\phi_3$;

Y is $F_3CSO_3^-$, $BF_4^-$, $PF_6^-$; and wherein $\phi$ is phenyl;

Me is methyl; and

Et is ethyl.

Other preferred catalysts are those having the formula $MX$, $ML_2$ and $ML_3$, wherein M, X and L are the same as defined above.

The ligand systems of the catalyst of this invention are not critical to either product yields or product distribution providing they are of a labile nature. The primary role of the ligand is to compliment the electronic configuration of the metal, to stabilize the complex and to aid in the solubilization of the metal component.

In the above catalyst composition, while it is preferred that X is a halogen and L is a phosphine moiety ($-PR_3$, wherein $PR_3$ is a trialkyl, triaryl or a mixed phosphine), X may also be $OAc^-$, $SCN^-$, $S_2O_3^-$, acetyl-acetonate, $S_2CNR_2^-$, $SC_6H_5^-$, $OC(S)OR^-$, $SnCl_3^-$, $CN^-$, $Mn(CO)_5^-$, $V(CO)_6^{31}$, $Mn(CO)_4 L^-$, $Mn(CO)_5X^-$ (wherein $X=Cl^-$, $Br^-, I^-$), $Os_3(CO)_{12}^-$, $Ir(CO)_3P\phi_3^-$, $M(CO)_3C_p^-$ (wherein $M=Cr$, Mo or W), $Co(CO)_4^-$, $PtX(P\phi_3)_2^-$ (wherein $X=Cl^-$, $Br^-$, $I^-$);

L may also be $P\phi_3$, $PMe\phi_2$, $PMe_2\phi$, $PMe_3$, $PEt_3$, $P_n-Bu_3$, $As\phi_3$, $AsEt_3$, $Sb\phi_3$, $P(p-ClC_6H_4)_3$, $P(OC_6H_4CH_3)_3$, $P(C_6H_{11})_3$, $OP(OEt)_3$, $P(O_n-Bu)_3$, $NH_3$, $NR_3$, diars, diphos, $CNC_6H_5$, $P-CH_3C_6H_4NC$, $P-CH_3OC_6H_4NC$, an olefin, alkyne, or $NC_5H_5$; and Y may be $F_3CSO_3^-$, $BF_4^-$, $PF_6^-$, $ClO_4^-$, $B\phi_4^-$, $I^-$, $Cl^-$, $Br^-$, $AlCl_4^-$ or a picrate.

In the above catalyst formula, when Y is a halogen, X cannot be a halogen, and n equals 2 or 4.

The catalyst of this invention may be dissolved in the reaction medium as a homogeneous catalyst, slurried in the reaction medium as an insoluble, unsupported heterogeneous catalyst, or in some cases where advantageous it may be supported on carriers such as silica, alumina or polymeric materials and slurried in the reaction medium. It is preferred, however, that the catalyst system be a homogeneous system where the catalyst is soluble in the reaction solvent. Catalysts insoluble in the reaction medium, however, are also useful if sufficient agitation and contact time are maintained.

The concentration of the catalyst in the solvent medium may range from $10^{-6}$ to 1 mole per liter and more preferably the catalyst concentration may range from about $10^{-1}$ to $10^{-5}$, most preferably $10^{-4}$ to $10^{-2}$ mole per liter.

The catalyst of this invention may be prepared by known techniques. For example, when M is Au, the catalyst may be prepared by generating the monovalent gold species from gold metal and isolating prior to dissolution.

Another technique for generating Au-containing catalysts is described as follows: Gold (I) halide is reacted with appropriate ligand (L) to give $X AuL_n$ in situ. Subsequently, if desired, the addition of AgY generates the corresponding ionic analog $[AuL_n]Y_z$. Metathetical reactions allow formation of the desired variations of X starting with either XAu or $XAuL_n$, or variations in Y starting with $[AuL_n]Y_z$. Species of the form $[AuL_n]Y$ are generated in situ by treatment of XAu with Ag Y, where L is the reactant olefin. The yields of catalyst based on the starting amount of gold metal are generally quite high as the reactions approach stoichiometric ratios.

There is evidence to suggest that temperature conditioning of gold containing catalysts enhances both the performance and stability of the catalysts since there appears to be an induction period required to generate the activated complex of the catalysts. This can be accomplished by gradually increasing the temperature of the catalyst solution from 50° C. to 200° C. over a period of time ranging from 2 to 24 hours, or more preferably, raising the temperature from 100° C. to 150° C. over a period of at least 6 hours.

The gross reaction product obtained by the inventive process is composed primarily of indene, styrene, and alpha-methylstyrene. Indene can be recovered from the gross reaction product by conventional techniques such as fractional distillation, extraction and low temperature fractional crystallization.

In addition to being used as a monomer in the making of various addition polymers, indene also finds use as a solvent.

EXAMPLES

The following working examples are presented to more thoroughly illustrate the present invention.

EXAMPLE 1

$[Au(PEt_3)]F_3CSO_3$ is prepared from the reaction of equimolar amounts of $[ClAu(PEt_3)]$ and $AgF_3CSO_3$ in benzene under a nitrogen atmosphere ($PEt_3$=triethylphosphine). After 1 hour of stirring, the resultant AgCl is separated. The filtrate serves as both catalyst and reaction medium. This solution is transferred to a stainless steel reaction vessel fitted with a septum and ball valve and previously charged with 10 psi of 60 mole % propylene/40 mole % $O_2$. The reaction vessel is subsequently placed in a heating block preheated to 200° C. and allowed to react for two hours. At this point the solution is cooled to room temperature and sampled through the septum via gas chromatography. Propylene conversion is found to be greater than 75% and the major products are identified by gas chromatograph/mass spectrometry as indene, styrene and methylstyrene in yields of 15% to 20% each. The solution shows no evidence of catalyst decomposition.

EXAMPLE 2

Example 1 is repeated except that, prior to the introduction of the reaction solution and after the introduction of 10 psi of 60 mole % propylene/40 mole % $O_2$, the reaction vessel is charged with 10 psi CO. The major reaction products are again identified by gas chromatography/mass spectrometry as indene, styrene and methylstyrene, but the yields are decreased by approximately 50%. This result indicates that CO is competing for the active sites on the metal and illustrates the importance of excluding coordinating ligands in these systems in accordance with the preferred embodiment of the invention.

Although only a few embodiments of the present invention have been described above, many modifications can be made without departing from the spirit and scope of the invention. All such modifications are intended to be included within the scope of the present invention which is to be limited only by the following claims:

We claim:

1. A process for producing indene comprising contacting benzene and propylene together in a liquid medium containing a transition metal complex of a metal selected from the group consisting of Au, Ag, Rh, Ir, Hg, Ni, Cu, Ru, Pt, Pd and Os.

2. The process of claim 1 wherein said catalyst is selected from the group consisting of $$[X_m M L_n][Y]_z$$

wherein
- M is a neutral, unipositive or dipositive metal selected from the group consisting of Au, Ag, Rh, Cu, Ir, Hg, Ni, Ru, Pt, Pd and Os;
- X is a uninegative coordinating anion;
- L is a neutral coordinating $\pi$-acid type ligand;
- Y is a uninegative non-coordinating anion; and wherein when
M is neutral, $n=1-6$; and wherein when
M is unipositive, $z=0$ or 1; $m=0$ or 1; $m+z=1$; and $n=1$ to 4; and wherein when
M is dipositive, $z=0$, 1 or 2; $m=0$, 1 or 2; $m+z=2$; and $n=0$ to 6.

3. The process of claim 2 wherein M is unipositive.

4. The process of claim 3 wherein M is Au.

5. The process of claim 4 wherein said catalyst is ionic.

6. The process of claim 5 wherein n equals 1.

7. The process of claim 6 wherein L is a phosphine.

8. The process of claim 7 wherein said catalyst is [Au(PEt$_3$)]F$_3$CSO$_3$ wherein PEt is triethylphosphine.

9. The process of claim 2 wherein M is a unipositive transition metal selected from the group consisting of Au, Ag, Rh, Cu, Ir and Hg.

10. The process of claim 2 wherein M is a dipositive metal selected from the group consisting of Ni, Cu, Ru, Pt, Pd and Os.

11. The process of claim 2 wherein said catalyst has the formula MX.

12. The process of claim 2 wherein said catalyst has the formula ML$_2$.

13. The process of claim 2 wherein said catalyst has the formula ML$_3$.

* * * * *